United States Patent [19]

Eagle et al.

[11] Patent Number: 5,229,103
[45] Date of Patent: Jul. 20, 1993

[54] ANTIPLAQUE MOUTHWASH CONCENTRATE

[75] Inventors: Scott Eagle, Long Branch; Graham Barker, Fair Lawn, both of N.J.

[73] Assignee: Hydrodent laboratories, Inc., Woodbridge, N.J.

[21] Appl. No.: 876,519

[22] Filed: Apr. 30, 1992

[51] Int. Cl.$^5$ .............. A61K 7/16; A61K 7/24
[52] U.S. Cl. ....................... 424/49; 424/55; 424/56
[58] Field of Search .............. 424/49, 55, 56

[56] References Cited

U.S. PATENT DOCUMENTS 3,947,570  3/1976  Penasak et al. ............ 424/49
4,657,758  4/1987  Goldemberg et al. ....... 424/49

Primary Examiner—Thurman K. Page
Assistant Examiner—James M. Spear
Attorney, Agent, or Firm—Omri M. Behr; Matthew J. McDonald

[57] ABSTRACT

There are provided shelf stable liquid concentrates for dilution to form dental rinse compositions for loosening and removing plaque present on dental surfaces, while reducing the level of plaque forming bacteria present in the oral cavity consisting essentially of an aqueous or an aqueous and alcoholic carrier for the ingredients of said concentrate, wherein the ingredients include about 0.1% to about 10% by weight of said concentrate of an oral surfactant, suitably an anionic surfactant, at least about 1% by weight of said concentrate of sodium benzoate, and sufficient pharmaceutically acceptable acid to maintain the pH of said concentrate in the range of about 6.2 to about 5.6. These concentrates, in order to be used, are diluted to form dental rinse compositions, with water, in the ratio of between about 1 to about 15 parts by weight of water to 1 part by weight of concentrate, resulting in a pH in the range of about 6.0 to about 4.7. There is also provided a method of loosening and removing plaque present on dental surfaces, while reducing the level of plaque forming bacteria present in the oral cavity comprising the step of rinsing the oral cavity with such a composition.

13 Claims, No Drawings

ANTIPLAQUE MOUTHWASH CONCENTRATE

FIELD OF THE INVENTION

The invention relates to a shelf stable liquid concentrate for dilution to form a dental rinse composition for loosening and removing plaque present on dental surfaces, while reducing the level of plaque forming bacteria present in the oral cavity.

BACKGROUND OF THE INVENTION

Dental rinses are well known in the art of dental hygiene. Such rinses can be formulated for several different purposes, for example, the retardation of tooth decay by the addition of fluoride, the loosening or removal of plaque, the removal of mouth odor, and the reduction of the level of various bacteria resident in the oral cavity. Some of these desirable characteristics can be combined in a single rinse, some cannot be combined, or cannot be combined without secondary problems because of interaction of the various components which are required to carry out the various desired activities.

A highly successful and accepted dental rinse for the loosening of plaque, which renders it more amenable to removal during brushing with a conventional dentifrice is disclosed in U.S. Pat. No. 4,657,758 to Goldemberg, et al., the disclosure of which is incorporated herein by reference. This patent discusses a commercial product known by the trademark of Plax (manufactured by Oral Research Laboratories). The Plax rinse comprises, among other components well recognized in the art, an oral surfactant, preferably sodium lauryl sulfate, sodium benzoate which has been found to be effective in increasing the amenability of plaque to removal and an effective amount of detergent builder. The entire composition, which is sold in a dilution level at which it may be readily used by the purchaser is formulated to have a pH of from about 7.5 to about 10, preferably about 9.0. In order for the composition to be effective, the presence of a detergent builder is indicated as being essential. Furthermore, in order for the solution to be shelf stable, the pH must be held at the levels indicated, to prevent hydrolysis of the sodium lauryl sulfate. Goldemberg indicates that the presence of sodium benzoate increases the effectiveness of the composition. Goldemberg further indicates that sodium benzoate might have some anti-microbial properties. The literature however, indicates that such anti-microbial properties would be quite minimal at the pH levels of Plax.

Sodium benzoate per se has negligible anti-microbial properties. Benzoic acid however, has anti-microbial properties and these increase inversely with the degree of disassociation thereof. Clearly, sodium benzoate is substantially totally disassociated. The degree of disassociation of benzoic acid can be set forth as follows:

| pH* | 2 | 3 | 4 | 4.5 | 5 | 6 | 7 |
|---|---|---|---|---|---|---|---|
| Undisassociated Acid | 99 | 94 | 60 | 30 | 13 | 15 | 0.15 |

*Manufacturing Chemist & Aerosol News Oct. 1969 p. 35

Since, as stated, the anti-microbial activity of benzoic acid is directly proportional to the amount of undisassociated molecule in the solution, it is clear that at the pH's listed by Goldemberg the anti-microbial activity due to sodium benzoate is negligible. This is impliedly acknowledged by Goldemberg who utilizes other and additional anti-microbial agents to attempt to achieve this effect.

Regrettably, it is not possible to merely lower the pH of the Plax composition to the minimum level for effectiveness of the benzoate moiety, that is to say, 5.5 or lower because such solutions would not be shelf stable.

It would therefore be desirable to formulate a solution which achieves the plaque loosening and removal properties of Plax, while having substantially increased anti-microbial activity.

SUMMARY OF THE INVENTION

There is provided a shelf stable liquid concentrate for dilution to form a dental rinse composition for loosening and removing plaque present on dental surfaces, while reducing the level of plaque forming bacteria present in the oral cavity. Previously available mouth washes were either useful to reduce bacterial levels or loosen/remove plaque. Heretofore it was not known how to combine these two desirable properties in one effective shelf stable composition. Anti bacterial compositions generally require an acidic pH, suitably below 5.6. Unfortunately plaque loosening or removal compositions are not shelf stable at these levels, pHs of at least 7.5 being preferred.

Applicants have found that shelf stable concentrates can be formulated at pH levels of about 5.6–about 6.2. Contrary to expectations, when such concentrates are diluted with neutral water (pH about 7.0), the resultant pH of the diluate DROPS to between 4.7 and 6.0 depending on the initial pH and the degree of dilution.

The novel concentrates consist essentially of an aqueous or an aqueous and alcoholic carrier for the ingredients of said concentrate. The ingredients include about 0.1% to about 10%, by weight of said concentrate, of an oral surfactant, at least about 1% weight of said concentrate, of sodium benzoate and sufficient pharmaceutically acceptable acid to maintain the pH of said concentrate in the range of about 6.2 to about 5.6. They are devoid of detergent builders.

The dental rinse compositions are obtained when the concentrate is diluted with water in the ratio of between about 1 to about 15 parts by weight of water to 1 part by weight of concentrate to yield a pH in the range of about 6.0 to about 4.7.

There is also provided a method of loosening and removing plaque present on dental surfaces, while reducing the level of plaque forming bacteria present in the oral cavity comprising the step of rinsing the oral cavity with either such a dental rinse composition or by placing the concentrate in a suitable spray apparatus. An apparatus which does not require pre-dilution before use is especially desirable. Such apparatus as are disclosed in U.S. Pat. Nos. 4,564,005 and 4,979,503, the disclosure of which is incorporated by reference.

DESCRIPTION OF THE PREFERRED EMBODIMENTS

The concentrates of the present invention comprises between 0.1 to about 10%, suitably about 0.5 to about 2.5% by weight of said concentrate of an oral surfactant. Any surfactant approved for such use may be utilized. There may be utilized one surfactant or a mixture of surfactants, the surfactants may be non-ionic or anionic. It has been found particularly suitable to utilize, as surfactant, sodium lauryl sulfate in conjunction with a non-ionic surfactant for example, Poloxamer 128 (registered trademark and manufactured by BASF-Wayandotte). Where such mixtures are utilized it is desirable to utilize between about 2 to about 3% by weight of the concentrate of the sodium lauryl sulfate in conjunction with from about 0.5 to about 2% of the non-ionic surfactant.

The composition further comprises sodium benzoate in a concentration of at least about 1%, suitably from about 1 to 10% by weight of the concentrate. Additional components comprise conventional additives such as specially denatured alcohol, suitably in a range of from about 5 to about 20% by weight of the concentrate, sweeteners such a sodium saccharine and conventional flavorants and colorants.

Additionally, there is added sufficient pharmaceutically acceptable acid to maintain the pH of the concentrate in the range of about 6.2 to about 5.6. As stated hereinabove, it is Applicants surprising finding that when the composition of the present invention is diluted from a ratio of one part by weight of concentrate through 15 parts by weight of water to 1 part concentrate, the pH of the diluted solution does not rise but, in fact, drops. Since the pH of the diluting water is higher than the pH of the concentrate Applicants have no reasonable explanation for this phenomenon.

The nature of the acid, in this environment, appears to be irrelevant. It occurs whether the acid is organic or inorganic and it occurs whether it is monobasic or polybasic. Citric acid, which is a tribasic acid is preferred. However, the phenomenon has equally been observed with acids as diverse as ascorbic, succinic, tartaric, malic, adipic, aspartic, lactic, gluconic, hydrochloric, acetic and phosphoric. Among the previously mentioned acids, in addition to citric acid, tartaric, phosphoric, and hydrochloric are considered to be desirable.

The compositions of the present invention may be utilized in one of two modes. The concentrate may be diluted in a conventional drinking vessel and utilized to rinse the mouth therewith. While this mode of utilization serves to loosen the plaque and further serves as an anti-microbial agent in the oral cavity, its plaque removal potential is not maximized. Such plaque removal potential can, of course, be increased by brushing the teeth with a dentifrice immediately after use. On the other hand, the compositions may be used effectively not only as loosening, but also as removal agents if the concentrate is placed in the apparatus disclosed hereinabove in U.S. Pat. Nos. 4,564,005 and 4,979,503 in which a jet of the diluted concentrate is directed against the tooth enamel and serves to remove plaque therefrom. It has previously been stated that compositions of the foregoing nature are not shelf stable at pH's much below 6, 5.6 being a substantially lower limit of shelf stability. It should be stressed that the operative term here is "shelf stability". The amount of deterioration of the concentrate when diluted immediately before use is negligible, problems with deterioration would only occur were such solutions to be kept for a month or more.

Experiments have been carried out demonstrate the drop in pH with a single acid (citric acid) and varying concentrations of sodium benzoate and sodium lauryl sulfate. Similarly experiments have been carried out to show the drop in pH upon dilution using different acids and a constant amount of the sodium benzoate, sodium lauryl sulfate and other concentrate constituents.

In vitro tests were also carried out to determine the inhibition of diluted (9:1) concentrate against *Streptococcus mutans* and *Actinomyces viscosus* as compared to certain other commercially available mouthwashes.

EXAMPLE 1

Concentrate Formulation

Concentrate preformulations are prepared in accordance with the following table. Hereinbelow all compositions within the scope of this invention are referred to as Hydrodent.

| | HYDRODENT FORMULAS | | | |
|---|---|---|---|---|
| Ingredient | Formula I % (wt) | Formula II % (wt) | Formula III % (wt) | Formula IV % (wt) |
| Sodium Benzoate | 1.1 | 1.4 | 4.1 | 8.7 |
| Sodium Lauryl Sulfate | 2.0 | 2.2 | 2.1 | 2.6 |
| SDA Alcohol | 5.0 | 15.0 | 13.0 | 18.0 |
| Sodium Saccharine | .2 | .3 | .3 | .4 |
| Non-ionic Surfactant | .5 | .9 | 1.3 | 1.9 |
| Flavor | .7 | .9 | .8 | .7 |
| Water | 90.5 | 79.3 | 78.4 | 67.7 |

Sufficient citric acid is then added to bring the pH into the range of 6.2 to 5.6. In accordance with the above formulation, but using, in place of citric acid, tartaric, phosphoric or hydrochloric acids similar results are obtained.

EXAMPLE 2 pH Ranges of diluted Hydrodent concentrates

The concentrates tested below correspond to the constituents of Formula II of Example 1 above wherein the amounts of sodium benzoate and sodium lauryl sulfate are varied as set forth below. The amount of citric acid added is that sufficient to give the indicated starting pH in each of the sub-experiments.

| Effect of Various Organic and Inorganic Acids on pH of Diluted Hydrodent Concentrates | | | | |
|---|---|---|---|---|
| ACID | ORIGINAL pH | 1:9 | 1:15 | 1:20 |
| ASCORBIC | 6.20 | 5.27 | 5.26 | |
| | 5.80 | 4.81 | 4.78 | |
| | 5.60 | 4.62 | 4.58 | 4.51 |
| SUCCINIC | 6.40 | 5.65 | 5.62 | 5.64 |
| | 6.15 | 5.44 | 5.40 | 5.43 |
| | 5.80 | 5.06 | 5.00 | 4.99 |
| CITRIC (as control and double control) | 5.93 | 5.23 | | |
| TARTARIC | 6.31 | 5.40 | 5.38 | 5.36 |
| | 6.02 | 5.20 | 5.20 | 5.21 |
| | 5.78 | 5.00 | 4.95 | |
| MALIC | 6.27 | 5.47 | 5.48 | 5.50 |
| | | 5.39 | 5.40 | 5.50 |
| | 5.85 | 4.97 | 4.97 | 5.00 |
| ADIPIC | 6.40 | 5.98 | 6.11 | 6.20 |
| | 5.86 | 5.27 | 5.31 | 5.40 |
| ASPARTIC (Amino acid dissolves slowly pH drifts down as acid dissolves) | 5.80 | 5.01 | 5.04 | 5.11 |
| LACTIC ACID | 6.35 | 6.03 | 6.14 | 6.27 |
| | 5.85 | 5.27 | 5.34 | 5.48 |
| GLUCONIC ACID | 6.32 | 5.93 | 6.06 | 6.10 |
| | 5.96 | 5.27 | 5.30 | 5.45 |
| | 5.76 | 4.98 | 5.63 | 5.11 |
| HYDROCHLORIC ACID | 6.60 | 5.84 | | |
| | 6.38 | 5.55 | | |
| | 6.15 | 5.33 | | |
| | 5.98 | 5.12 | | |

-continued

Effect of Various Organic and Inorganic Acids on pH of Diluted Hydrodent Concentrates

| ACID | ORIGINAL pH | 1:9 | 1:15 | 1:20 |
|---|---|---|---|---|
|  | 5.80 | 5.02 |  |  |
|  | 5.60 | 4.75 | 4.70 |  |
| ACETIC ACID | 6.51 | 5.81 |  |  |
|  | 6.40 | 5.62 |  |  |
|  | 6.00 | 5.180 |  |  |
|  | 5.60 | 4.78 |  |  |
| PHOSPHORIC ACID | 6.82 | 5.77 |  |  |
|  | 6.61 | 5.55 |  |  |
|  | 6.40 | 5.33 |  |  |
|  | 6.21 | 5.18 |  |  |
|  | 6.00 | 4.98 |  |  |
|  | 5.79 | 4.74 |  |  |
|  | 5.60 | 4.55 |  |  |

EXAMPLE 3

Relationship of pH to Composition

The pH of the diluted concentrates depend on the dilution rates as well as the percent of Sodium benzoate and sodium lauryl sulfate in the original Concentrate. Citric acid used in all cases.

a: Concentrate with 1.35% Sodium Benzoate and 2.15% Sodium Lauryl Sulfate

| Dilution Rate: | 5:1 | 9:1 | 15:1 | 20:1 |
|---|---|---|---|---|
| pH (original 6.1) | 5.3 | 5.36 | 5.43 | 5.50 |
| Dilution Rate: | 5:1 | 9:1 | 15:1 | 20:1 |
| pH (original 5.6) | 4.95 | 4.91 | 4.91 | 4.94 | b: Concentrate with 2% Sodium Benzoate and 1.79% Sodium Lauryl Sulfate

Original pH 6.0 at a dilution rate of 9:1 drops to 5.3.

c: Concentrate with 12.25% Sodium Benzoate and 3.50% Sodium Lauryl Sulfate

Original pH 6.1 at a dilution rate of 13:1 pH drops to 4.9 d: Concentrate with 1.35% Sodium Benzoate and 1.79% Sodium Lauryl Sulfate

Original pH 6.03 at dilution rate of 9:1    pH drops to 5.26
Original pH 5.52 at a dilution rate of 9:1    pH drops to 4.70 e: Concentrate with 1.0% Sodium Benzoate and 1.79% Sodium Lauryl Sulfate

Original pH at 6.20 at a dilution rate of 9:1 drops to 5.27
Dilution with alkaline tap water (pH 7.6)

| DILUTION RATE | pH | DIL'N RATE | pH | DIL'N RATE | pH | DIL'N RATE | pH |
|---|---|---|---|---|---|---|---|
| 1:1 | 6.04 | 7:1 | 5.51 | 13:1 | 5.53 | 19:1 |  |
| 2:1 | 5.80 | 8:1 | 5.49 | 14:1 | 5.53 | 20:1 | 5.63 |
| 3:1 | 5.68 | 9:1 | 5.49 | 15:1 |  | 21:1 |  |
| 4:1 | 5.61 | 10:1 | 5.48 | 16:1 | 5.55 | 22:1 |  |
| 5:1 | 5.56 | 11:1 | 5.48 | 17:1 |  | 23:1 |  |
| 6:1 | 5.53 | 12:1 | 5.50 | 18:1 | 5.58 | 24:1 | 5.78 |

Note: All dilutions (a–d) were with deionized water.

EXAMPLE 4

Laboratory plaque removal assay using *Streptococcus mutans*

Tests were carried out on the formulation of Formula II of Example 1 (diluted 1:9), to determine the plaque removal characteristics as compared to those of commercially available mouth rinses.

TABLE 4:1

Visual Estimates of Adherent *streptococcus mutans* Plaque

| Product | Visual Scores | | Mean | |
|---|---|---|---|---|
|  | Before | After | Before | After |
| Hydrodent | 5,5,4,2 | 2,3,1,1 | 4.00 | 1.75 |
| Listerine | 4,4,4,3 | 2,3,2,1 | 3.75 | 2.00 |
| Peridex | 3,4,4,5 | 1,2,2,3 | 4.00 | 2.00 |
| Plax (mint) | 3,5,4,4 | 1,3,3,2 | 3.50 | 2.25 |
| Water | 3,5,4,4 | 3,3,3,3 | 4.00 | 3.00 |

An analysis of variance was performed on the above data to determine if significant differences existed between the products tested. The results of the ANOVA are presented in below.

TABLE 4:2

| Between | 9 | 31.730 | 3.5300 | 4.55 |
|---|---|---|---|---|
| Within | 30 | 23.250 | .7750 |  |

A statistical Turkey post hoc test was then performed to determine where significant differences occurred. Only the Hydrodent solution decreased visual scores between the before and after treatments ($p < 0.05$). Data for plaque weights are presented below.

TABLE 4:3

| Product | Plaque Weights | |
|---|---|---|
|  | Individual Values (mg) | Mean (mg) |
| Hydrodent | 11, 11, 5, 4 | 7.75 |
| Listerine | 10, 10, 5, 6 | 7.75 |
| Peridex | 8, 5, 7, 3 | 5.75 |
| Plax | 5, 11, 13, 12 | 10.25 |
| Water | 11, 8, 6, 8 | 8.25 |

An analysis of variance was performed on the previous data to determine if significant differences existed between the products tested. The results of the ANOVA are presented below.

| SOURCE | DF | SS | MS | F |
|---|---|---|---|---|
| Between | 4 | 41.20 | 10.300 | 1.1907 |
| Within | 15 | 129.75 | 8.649 |  |

There was no significant differences among the groups tested. Results for plaque glycolysis are presented below.

TABLE 4:5

| Plaque Glycolysis | | |
|---|---|---|
| Hydrodent | 6.30, 5.86, 6.85, 7.16 | 6.54 |
| Listerine | 4.23, 4.23, 4.28, 5.18 | 4.48 |
| Peridex | 7.27, 7.14, 7.20, 6.89 | 7.13 |
| Plax | 5.20, 4.68, 4.71, 4.83 | 4.86 |
| Water | 4.19, 4.14, 4.18, 4.21 | 4.18 |

An analysis of variance was performed on the previous data to determine if significant differences existed between the products tested. The results of the ANOVA are presented below.

TABLE 4:6

| Analysis of Variance of Glycolysis Data | | | |
|---|---|---|---|
| Source | DF | SS | MS | F |
| Between | 4 | 27.620 | 6.906 | 54.193 |
| Within | 15 | 1.912 | .137 |  |

The Hydrodent solution was significantly superior in retarding acid formation compared to Listerine, Plax and water at the level of p<0.001.

Conclusion: Hydrodent concentrate, tested at use concentrations, was consistently superior to Listerine and Plax in removing artificial plaque deposits and in significantly preventing acid formation in the adherent plaque after treatment.

EXAMPLE 5

Antimicrobial Effect: S. Mutans

Comparison of Hydrodent concentrate (Formula II of Ex. 1, diluted 1:9) with marketed U.S. products on inhibiting the growth of *Streptococcus mutans*, an organism associated with clinical caries.

A base layer of 7-8 ml of trypticase soy agar was applied to a sterile petri dish and allowed to set. Eight ml of seed layer containing a 1:10 dilution of A. viscosus was poured onto the base layer. Sterile penicylinders were placed on the top layer of agar and 0.20 ml of each test material was placed into the penicylinders. The petri dishes were then incubated for 24 hours at 37° C. Zones of inhibition for each test material were measured in mm.

TABLE 5:1

| MATERIALS | # TESTS | ZONES (mm) | MEAN |
|---|---|---|---|
| Hydrodent | 4 | 23, 23, 24, 24 | 23.5 |
| Peridex | 4 | 21, 21, 20, 20 | 20.5 |
| Plax | 4 | 15, 14, 14, 14 | 14.25 |
| Listerine | 4 | 6, 6, 6, 6 | 6.0 |
| Viadent | 4 | 11, 11, 11, 11 | 11.0 |
| Water | 4 | 0, 0, 0, 0 | 0 |

An analysis of variance was performed on the above data to determine if significant differences existed between the products tested. The results of the ANOVA are presented below.

TABLE 5:2

| SOURCE | df | SS | MS | F |
|---|---|---|---|---|
| Between | 5 | 1555.21 | 311.04 | 2035.91* |
| Within | 18 | 2.75 | .15 | |

*$p < .01$

A statistical Tukey post hoc test was then conducted on the data to find specific differences. It was found that the Hydrodent concentrate was statistically superior to all other products tested (0.01). Other statistical differences (0.01) between products were Peridex>Listerine, Plax and Viadent; Plax>Viadent>Listerine; Viadent>Listerine. Water was ineffective.

EXAMPLE 6

Antimicrobial Effect: Actinomyces viscosus

Comparison of Hydrodent concentrate (Formula II of Ex. 1, diluted 1:9) with marketed U.S. products on inhibiting the growth of *Actinomyces viscosus* an organism associated with clinical caries.

A base layer of 7-8 ml of trypticase soy agar was applied to a sterile petri dish and allowed to set. Eight ml of seed layer containing a 1:10 dilution of *Actinomyces viscosus* was poured onto the base layer. Sterile penicylinders were placed on the top layer of agar and 0.20 ml of each test material was placed into the penicylinders. The petri dishes were then incubated for 24 hours at 37° C. Zones of inhibition for each test material were measured in mm.

TABLE 6:1

| MATERIALS | # TESTS | ZONES (mm) | MEAN |
|---|---|---|---|
| Hydrodent | 3 | 17,15,17 | 16.33 |
| Peridex | 4 | 18,18,19,19 | 18.5 |
| Plax | 4 | 11, 11, 11, 11 | 11. |
| Listerine | 4 | 5, 5, 5, 6 | 5.25 |
| Viadent | 4 | 12, 12.5, 13, 12.5 | 12.5 |
| Water | 4 | 0, 0, 0, 0 | 0 |

An analysis of variance was performed on the above data to determine if significant differences existed between the products tested. The results of the ANOVA are presented below.

TABLE 6:2

| SOURCE | df | SS | MS | F |
|---|---|---|---|---|
| Between | 5 | 925.8 | 185.2 | 640.23* |
| Within | 17 | 4.92 | .29 | |

*$p < .01$

A statistical Schefe post hoc test was then conducted on the data to find specific differences. It was found that Peridex was statistically superior to all other products tested (0.01) level. Hydrodent composition was statistically superior to all other products tested (0.01) level except Peridex. Other statistical differences (0.01) between products were Plax and Viadent>Listerine. Water was ineffective.

CONCLUSION: Both Peridex and Hydrodent composition were superior to the other products tested for inhibiting the growth of *A. viscosus*. Only Peridex was superior to Hydrodent in this study.

We claim:

1. A shelf stable liquid aqueous or aqueous/alcoholic concentrate for dilution to form a dental rinse composition for loosening and removing plaque present on dental surfaces, while reducing the level of plaque forming bacteria present in the oral cavity having ingredients consisting essentially of: about 0.1% to about 10% by weight of said concentrate of an oral surfactant, at least about 1% by weight of said concentrate of sodium benzoate and sufficient pharmaceutically acceptable acid to maintain the pH of said concentrate in the range of about 6.2 to about 5.6.

2. The concentrate of claim 1 wherein said surfactant is an anionic surfactant.

3. The concentrate of claim 2 wherein said surfactant is sodium lauryl sulfate.

4. The concentrate of claim 1 wherein said acid is an organic acid.

5. The concentrate of claim 1 wherein said acid is an inorganic acid.

6. The concentrate of claim 1 wherein said acid is a polybasic acid.

7. The concentrate of claim 1 wherein said acid is selected from the group consisting of citric, tartaric, phosphoric and hydrochloric acids.

8. The concentrate of claim 1 which comprises between about 1% and about 10% by weight of sodium benzoate.

9. The concentrate of claim 1 which comprises between about 0.5% and about 2.5% by weight of oral surfactant.

10. A dental rinse composition for loosening and removing plaque present on dental surfaces, while reducing the level of plaque forming bacteria present in the oral cavity consisting essentially of a concentrate of claim 1 when diluted with water in the ratio of between about 1 to about 15 parts by weight of water to 1 part by weight of concentrate.

11. The rinse composition of claim 10 having a pH in the range of about 5.6 to about 4.6.

12. A method of loosening and removing plaque present on dental surfaces, while reducing the level of plaque forming bacteria present in the oral cavity comprising the step of rinsing the oral cavity with a composition of claim 10.

13. A method of loosening and removing plaque present on dental surfaces, while reducing the level of plaque forming bacteria present in the oral cavity comprising the step of rinsing the oral cavity with a composition of claim 11.

* * * * *